United States Patent [19]

Fosker et al.

[11] 4,127,570
[45] Nov. 28, 1978

[54] β-AMINOPENICILLINS, SALTS AND ESTERS

[75] Inventors: George R. Fosker, Horsham, England; William Davies, Edinburgh, Scotland

[73] Assignee: Beecham Group Limited, England

[21] Appl. No.: 413,862

[22] Filed: Nov. 8, 1973

Related U.S. Application Data

[62] Division of Ser. No. 182,135, Sep. 20, 1971, abandoned.

[30] Foreign Application Priority Data

Sep. 25, 1970 [GB] United Kingdom ............... 45704/70

[51] Int. Cl.$^2$ ............................................ A61K 31/43
[52] U.S. Cl. .................................. 260/239.1; 424/271
[58] Field of Search ...................... 260/239.1, 239.1 A

[56] References Cited

U.S. PATENT DOCUMENTS

| 3,120,514 | 2/1964 | Doyle et al. .................. 260/306.7 C |
| 3,385,847 | 5/1968 | Vanderhaeghe et al. .... 260/239.1 A |
| 3,898,217 | 8/1975 | Aellsiept et al. .................. 260/239.1 |
| 3,904,604 | 9/1975 | Lee et al. .......................... 260/239.1 |
| 3,954,730 | 5/1976 | Metzer .............................. 260/239.1 |

Primary Examiner—Nicholas S. Rizzo
Attorney, Agent, or Firm—Jacobs & Jacobs

[57] ABSTRACT

β-Aminopenicillins, Salts and Esters are described having a wide spectrum of activity against Gram-positive and Gram-negative organisms. The β-aminopenicillins are derivatives of 6-amino-penicillanic acid and the procedure for preparing the β-aminopenicillins is set forth. β-aminopenicillins are characterized by having in the 6-position side chain a cycloalkyl ring of 5 – 7 carbon atoms particularly cyclopentyl, cyclohexyl or cycloheptyl.

11 Claims, No Drawings

β-AMINOPENICILLINS, SALTS AND ESTERS

This application is a division of application Ser. No. 182,135, filed Sept. 20, 1971 now abandoned.

This invention relates to certain new penicillins and is particularly concerned with a new class of penicillins which are derivatives of 6-aminopenicillanic acid and which are of value as antibacterial agents, as nutritional supplements in animal food, as agents for the treatment of mastitis in cattle and as therapeutic agents in poultry and animals, including man, in the treatment especially of infectious diseases caused by Gram-positive and Gram-negative bacteria.

6-[D-α-aminophenylacetamido] penicillanic acid (or ampicillin) has proved an extremely valuable antibacterial agent, having as it does a relatively broad spectrum of activity against both Gram-positive and Gram-negative bacteria. In view of the valuable properties of ampicillin, many attempts have been made to prepare new penicillins having structures closely related to ampicillin, in the hope that these novel structures will exhibit the same or superior properties. Thus, British Pat. No. 1,057,028 describes 6-(β-amino-β-phenylpropionamido) penicillanic acid while our own British Patent Specification No. 1,133,448 describes structures of the type (I):

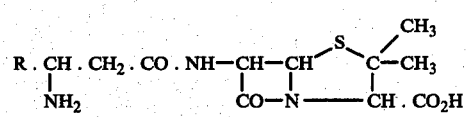

wherein R is a substituted phenyl group or heterocyclic group. British Pat. Nos. 960,896 and 962,943 describe inter alia penicillins of the formula (II):

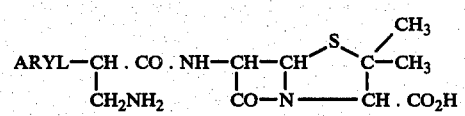

while Belgian Pat. No. 641,516 describes compounds of formula (III):

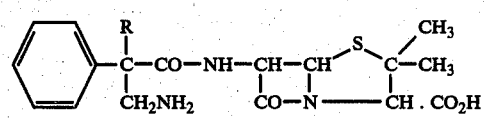

wherein the group R is alkyl, aryl or aralkyl.

Some of these known β-aminopenicillins approach the antibacterial activity of ampicillin in vitro but there is no evidence that they are useful oral drugs. For example, Betacin (the D-epimer of II; Aryl = phenyl) is said to give only poor oral blood levels in man (Current Therap. Res., 1965, 7, 226).

This invention is based upon the discovery of a class of β-amino penicillins which, upon oral administration, achieve higher and in some cases more prolonged blood levels than ampicillin. In general the new class of penicillins have a high level of activity against both Gram-positive and Gram-negative organisms, and thus many of these new compounds may offer therapeutic advantages over ampicillin.

According to the present invention there is provided a class of β-amino penicillins of formula (IV):

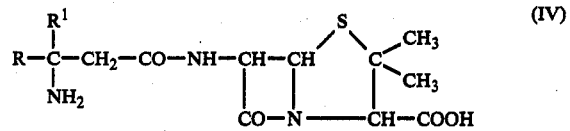

and non-toxic salts and hydrolysable esters thereof, in which formula R is a $C_1$ to $C_6$ straight or branched chain alkyl group, a $C_5$ to $C_7$ cycloalkyl or cycloalkenyl group; $R^1$ is hydrogen or a $C_1$ to $C_6$ alkyl group; or R and $R^1$ taken together represent a $C_4$ to $C_6$ alkylene group which may be interrupted by a hetero atom.

The salts of the penicillins of formula (IV) are non-toxic salts including non-toxic metallic salts such as sodium, potassium, calcium and aluminium, ammonium and substituted ammonium salts, e.g. salts of such non-toxic amines as trialkylamines (including triethylamine), procaine, dibenzylamine, N-benzyl-β-phenethylamine, 1-ephenamine, N,N¹-dibenzylethylenediamine, dehydroabietylamine, N,N¹-bis-dehydro-abietylethylenediamine, and other amines which have been used to form salts with benzylpenicillin. Acid addition salts of the compounds of formula (IV) are also included in the scope of this invention.

The esters of the penicillins of formula (IV) are non-toxic esters, particularly those known esters which are easily de-esterified in the body to give the parent penicillanic acids. Examples of such esters include acyloxyalkyl esters, particularly the acyloxymethyl esters such as acetoxymethyl and pivaloyloxymethyl esters.

By way of example in penicillins of formula (IV) R may be methyl, ethyl, n- or iso- propyl, n- sec- or tert-butyl, cyclopentyl, cyclohexyl, cycloheptyl, cyclohexenyl or cyclohexadienyl; $R^1$ may be hydrogen or a methyl or ethyl group. Alternatively R and $R^1$ taken together with the carbon atom to which they are attained may form a cyclopentyl, cyclohexyl or cycloheptyl ring which may be interrupted by an O, S atom or a group $>NR^2$ where $R^2$ represents hydrogen or a lower alkyl group such as methyl or ethyl.

Preliminary tests on representative members of the class of penicillins (IV) have shown the anticipated wide spectrum of activity against both Gram-positive and Gram-negative organisms. In general the compounds of this invention are antibacterially slightly less active in vitro than ampicillin, but surprisingly high blood levels have been achieved on oral administration to small mammals.

The present invention further provides a process for the preparation of penicillins having the general formula (IV) and salts and esters thereof in which 6-aminopenicillanic acid or a salt or ester thereof or the reaction product of 6-aminopenicillanic acid with an organo silicon compound is treated with a reactive derivative of an acid of the general formula (V):

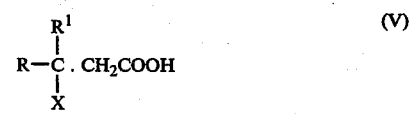

where R is as hereinbefore defined and X is a nitrogen-containing group which may subsequently be converted into a primary amino group. The term X particularly includes the so-called N-protected amino groups which can be found in the literature on peptide synthesis.

The conversion of the nitrogen-containing group X of the intermediate penicillin (VI)

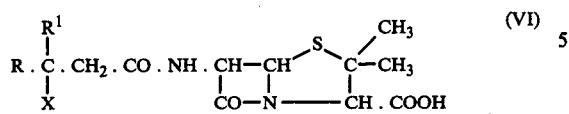

to a primary amino group may be effected by hydrogenation or hydrolysis it being understood that both steps must be carried out under conditions sufficiently mild that they do not disrupt the sensitive β-lactam ring. When the amino group is protected by protonation only, conversion of X to $NH_2$ merely requires adjustment of pH.

The reactive derivative of the acid (V) may be the acid halide, azide anhydride, mixed anhydride, or the reactive intermediate formed from the acid and a carbodiimide or carbonyldiimidazole.

Examples of the nitrogen-containing group X which, in the intermediate penicillin (VI), can be converted into the primary amino group by a process of catalytic hydrogenation include the azido group, the benzyloxycarbonylamino group, and substituted benzyloxycarbonylamino group.

Examples of the group X which may be converted into a primary amino group by a process of mild acid hydrolysis include enamine groups of general formula (VII), or tautomeric modifications thereof, and o-hydroxyarylideamino groups of the general formula (VIII), or tautomeric modifications thereof. More detailed descriptions of the use of these groups in the synthesis of amino-penicillins appear in British Patent Nos. 991,586 and 980,777:

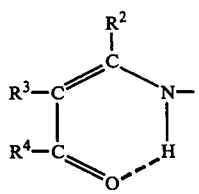
(VII)

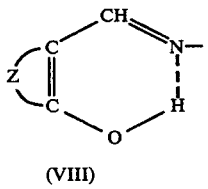
(VIII)

In structures (VII) and (VIII) the dotted lines represent hydrogen bonds. In structure (VII) $R^2$ is a lower alkyl group of 1 to 6 carbon atoms, an aryl group or a lower alkoxy group of 1 to 6 carbon atoms. In structure (VIII) Z represents the residue of a substituted or unsubstituted benzene or naphthalene ring.

In a still further process of the present invention the nitrogen-containing group X is a protonated amino group $NH_3^+$. In such a process the reaction of the 6-aminopenicillanic acid and the reactive acid derivative is best carried out in weekly acid medium, the free primary amino group being liberated at the end of the reaction by adjustment of the pH of the reaction mixture from acid to neutral or mildly alkaline.

The novel penicillins (IV) are capable of existing in two epimeric forms and it is to be understood that the invention includes both the D-and L- forms as well as the DL- mixture. They are also capable of existing in the anhydrous form or as hydrates of various degrees of hydration.

Certain embodiments of the invention will now be illustrated by the following specific Examples:

EXAMPLE I

Preparation of 6-[DL-2-amino-3-methyl butyl carbamido]-penicillanic acid.

Isobutyraldehyde (46 ml.), malonic acid (52 g) and ammonium acetate (77 g) were heated at reflux for 6 hours in 95% ethanol (150 ml.). The solution was allowed to cool, the crude product (25.5 g) collected by filtration and recrystallised from methanol-ether to give the pure amino acid (15.1 g. m.p. 194°).

The amino acid (6.5 g) was suspended in dry methylene dichloride (100 ml.) and dry hydrogen chloride gas passed for one hour. Thionyl chloride (7.6 ml.) was added to the suspension and gently refluxed for 4 hours. The resultant solution was clarified by filtration, evaporated to dryness under reduced pressure and the crude solid triturated with dry ether. The white solid was collected by filtration, quickly washed with dry ether and dried in vacuo over phosphorus pentoxide to give the acid chloride hydrochloride, [(6.15 g), i.r. γmax (mull.) 1800 cm$^{-1}$ acid chloride carbonyl], shown by analysis and spectra to be contaminated with 4–5% of the amino acid hydrochloride.

Solutions of the acid chloride hydrochloride (6.0 g) in methylene dichloride (100 ml.) and triethylamine (2.9 g) in methylene dichloride (25 ml.) were added concurrently over a period of 10 minutes to a solution of triethylammonium 6-amino penicillanate (9.15 g) in methylene dichloride (75 ml.) at 5°. After stirring the reaction mixture for one hour further, the white precipitated solid was filtered, well washed with methylene dichloride and dried in vacuo over phosphorus pentoxide to yield 6 [dl-2-amino-3-methyl butyl carbamido] penicillanic acid [(7.06 g) i.r. γmax (mull.) 1770 cm$^{-1}$ (β lactam CO, 1660 cm$^{-1}$ amide carbonyl]. This material, when subjected to paper chromatography in butanol:ethanol:water revealed a single zone of inhibition at an $R_f$ value of 0.19 and was estimated by colorimetric assay with hydroxylamine to be 59% pure.

EXAMPLE II

Preparation of 6-[(1-amino-cyclohexyl) acetamido]penicillanic acid

Cyclohexanone (49 g), malonic acid (52 g), and ammonium acetate (77 g) were heated at reflux for six hours in 95% ethanol (150 ml.). The solution was allowed to cool, the crude product (47 g) collected by filtration and recrystallised from 95% ethanol to yield (1-aminocyclohexyl) acetic acid [(40 g) m.p. 240° C.: (found C, 61.0; H, 9.7; N, 8.9; $C_8H_{15}NO_2$ requires C, 61:1; H, 9.6; N, 8.9%) n.m.r. δppm ($D_2O$) 1.5–1.8 (b.s., 10H), 2.5 (s, 2H), i.r.$v_{max}$ (mull) 2150 cm$^{-1}$ (s, $-NH_3^{(+)}$ overtone), 1610 and 1495 cm$^{-1}$ (s,s, $-NH_3^{(+)}$, 1560 cm$^{-1}$ (b.s. $-CO_2^{(-)}$)].

The amino acid (39.25 g) was suspended in dry methylene dichloride and dry hydrogen chloride gas passed through for 30 minutes. The white solid, (1-aminocyclohexyl) acetic acid hydrochloride [(46.8 g) m.p. 200°–204° C.; (found C, 49.6; H, 8.4; N, 7.2; Cl, 18.4; $C_8H_{16}ClNO_2$ requires C, 49.6; H, 8.3; N, 7.2; Cl, 18.3%] was collected by filtration, washed with dry methylene dichloride, dried in vacuo, and then added to a solution of thionyl chloride (27 ml.) in methylene dichloride (600 ml.). The suspension was heated gently at reflux for 2 hours to give a clear solution. The solvent was removed under reduced pressure, dry ether (500 ml.) was added, and evaporation was repeated under reduced pressure.

The partially crystalline residue was triturated with dry ether and collected by filtration to give the acid chloride hydrochloride [(41 g), m.p. 117° C.: (found Cl, 33.0; $C_8H_{15}Cl_2NO$ requires Cl, 33.8%) i.r. $\nu_{max}$ (mull) 1800 cm$^{-1}$ (s, —CO.Cl)].

Solutions of the acid chloride hydrochloride (23.3 g) in methylene dichloride (250 ml.) and triethylamine (14.0 ml.) in methylene dichloride (150 ml.) were added concurrently over a period of 20 minutes to a solution of triethylammonium 6-amino penicillanate (31.7 g) in methylene dichloride (250 ml.) at room temperature. Stirring was continued for a further 30 minutes, when the precipitated pale yellow solid was filtered, well washed with methylene dichloride and dried in vacuo to yield 6-[(1-aminocyclohexyl) acetamido]-penicillante, [(28.0 g), i.r. $\nu_{max}$ (mull) 1775 cm$^{-1}$ (s. β-lactam CO)]. This material, when subjected to paper chromatography in butanol: ethanol:water: 4:1:5 top layer, revealed a single zone of antibacterial activity at an $R_f$ value of 0.28 and was estimated by colorimetric assay with hydroxylamine to be 71% pure.

EXAMPLE III

Preparation of 6-[4-amino-1-thiacyclohexan-4-yl acetamido]penicillanic acid.

1-thiacyclohexan-4-one, (17.4 g), was added to malonic acid (17.1 g), and ammonium acetate, (23.1 g), in ethyl alcohol (300 ml.). This slurry was heated to give a solid mass which on further heating gave a suspension. Heating was continued for a further 4 hours at reflux and then filtered hot to give 4-amino-1-thiacyclohexan-4-yl acetic acid, [(14.17 g), m.p. 232°-235°(d), found C. 47.6; H, 7.5; N, 8.0; S, 18.6; $C_7H_{13}NO_2S$ requires C, 48.0; H, 7.5; N, 8.0; S, 18.3%].

The amino acid, (10 g), was suspended in dry methylene dichloride, (200 ml.), and dry hydrogen chloride gas passed for 30 minutes. The white amino acid hydrochloride, (11.8 g), was collected by filtration, washed with methylene dichloride dried in vacuo, and then added to a solution of thionyl chloride, (36 ml.), in methylene dichloride, (100 ml.), and gently refluxed for 30 minutes. The solvents were removed under reduced pressure, dry ether, (20 ml.), was then added and removed under reduced pressure twice. Finally dry ether was added and the crude acid chloride hydrochloride [(10.0 g), i.r. $\gamma_{max}$ (mull) 1795 cm$^{-1}$ acid chloride carbonyl], collected by filtration and dried in vacuo over phosphorus pentoxide.

The crude acid chloride hydrochloride, (1.8 g), was added to a solution of triethylammonium 6-aminopenicillanate (2.2 g), in methylene dichloride, (25 ml.), concurrently was triethylamine, (0.7 g). The reaction mixture was stirred for 1 hour, filtered, and the collected solid slurried with isopropanol and re-filtered to give the penicillin, [(1.05 g), i.r. $\gamma_{max}$. (mull) 1775 cm$^{-1}$ β lactam carbonyl]. When subjected to paper chromatography in butanol:ethanol: water, a single zone of antibacterial inhibition was obtained at an $R_f$ of 0.24 and it was estimated by colorimetric assay with hydroxylamine to be 40% pure.

EXAMPLE IV

Preparation of 6-[DL-2-amino (cyclohexan-1-yl) propionamido]penicillanic acid

Cyclohexane-1-aldehyde (56 g), malonic acid (52 g) and ammonium acetate (77 g) were heated at reflux for 24 hours in 95% ethanol (150 ml.). The solution was allowed to cool, the crude amino acid (41 g m.p. 219°-220°(d)) collected by filtration, washed with ethanol and dried in vacuo over phosphorus pentoxide. Recrystallisation from 5N. hydrochloric acid gave white needles of DL-β-amino-β-cyclohexyl propionic acid hydrochloride [(39 g) m.p. 214°-215°(d): (found C, 52.1; H, 8.9; N, 6.9; $C_9H_{18}ClNO_2$ requires C, 52.2; H, 8.7; N, 6.7%) n.m.r. δppm. [$(CD_3)_2SO$] 8.3 (3H, m), 3.3 (H,m), 2.7 (2H,d), 2.0–1.0 (11H, m), i.r. $\gamma_{max}$ (KBr) 3240 and 1600 (NH), 2600 (NH$^+$), 1710 cm$^{-1}$ (CO)].

The amino acid hydrochloride (6.2 g) was suspended in dry methylene dichloride (75 ml.) and dry hydrogen chloride gas passed for 30 minutes at 50°. Phosphorus pentachloride (9.45 g) was added slowly and then stirred for one hour further, with exclusion of moisture to give a clear solution. Anhydrous acetone (75 ml.) was then carefully added with stirring and evaporated to dryness under reduced pressure after 30 minutes. The white residue was triturated with anhydrous diethyl ether, filtered and dried in vacuo over phosphorus pentoxide to give acid chloride hydrochloride [(6.81 g) i.r. $\gamma_{max}$ (mull) 2700 and 1900 (NH$^+$), 1790 (CO), 1600 cm$^{-1}$ (NH)].

A vigorously stirred, finely divided suspension of 6-amino penicillanic acid (prepared by dissolving triethylammonium 6-amino penicillanate, (6.35 g) in 25% aqueous acetone at $-5°$ and adjusting the pH to 2.5 with cold 5N hydrochloride acid) was treated portion wise with the acid chloride hydrochloride (6.75 g) with the reaction mixture maintained at pH 2.5 to 3.5 by the careful addition of triethylamine. After 30 minutes when the addition was complete, a clear solution was obtained. Stirring was continued for 20 minutes further at 0°-5° when the pH was readjusted to 4.5 with triethylamine and the acetone removed under reduced pressure. The pH was adjusted to 7.0 with triethylamine and the solution evaporated to dryness under reduced pressure. The resulting white solid was dried in vacuo over phosphorus pentoxide and then thoroughly triturated with dry methylene dichloride and filtered to give the required penicillin [(5.4 g), m.p. 170°(d), n.m.r. δp.p.m. [$(CD_3)_2SO$] 5.5 (2H, s); 4.2 (H.s); 3.1 (H, t); 2.75 (2H, m); 2.0–1.0 17H, m); i.r. $\gamma_{max}$ (mull) 3300 (NH); 1785 (lactam CO), 1660 cm$^{-1}$ (amide CO)]. The product, when subjected to paper chromatography in butanol:ethanol:water:: 4:1:5, (top layer), revealed a single zone of inhibition at an $R_f$ value of 0.44 and was estimated by colorimetric assay with hydroxylamine to be 78% pure.

EXAMPLE V

Preparation of 6-[DL-2-amino (cyclohex-1, 4-dien-1-yl) propionamido]penicillanic acid To a stirred solution of DL-β-amino-β-phenyl propionic acid (16.3 g) in liquid ammonia (800 ml.), tetrahydrofuran (200 ml.) and tertiary butanol (200 ml.) contained in a vacuum jacketed vessel, was added strips of lithium (8.0 g) over a period of 4 hours when a permanent blue colour was obtained. Ammonium chloride (62 g) was cautiously added and the ammonia allowed to slowly evaporate overnight. The white residue was dissolved in water (200 ml.), the volume reduced to about 50 ml. and the pH adjusted to 5.5. The white solid was collected and recrystallised from 5N. hydrochloric acid to give β-amino-β-cyclohex-1, 4-dienyl propionic acid hydrochloride [(15.0 g m.p. 210°-212°: (found C, 52.8; H, 7.0; N, 6.8; $C_9H_{14}ClNO_2$ requires C, 53.1; H, 6.9; N, 6.8%) n.m.r. δp.p.m. [$(CD_3)SO$] 9.0 (3H, m);

5.85 (H, s); 5.7 (2H, s)- 3.85 (H, t); 2.7 (6H, m) i.r. $\gamma_{max}$ (mull) 2600 and 1950 (NH$^+$), 1730 (CO), 1600 cm$^{-1}$ (C=C)].

The amino acid (6.1 g) was dissolved in 1.0N potassium hydroxide solution (60 ml.), the solution evaporated to dryness under reduced pressure and dried in vacuo over phosphorus pentoxide for 24 hours. The potassium salts was suspended in absolute ethanol (50 ml.), methylacetoacetate (3.48 g) added and the mixture gently refluxed for 2 hours. The clear solution was reduced to about 10 ml. and triturated with ether. The white crystalline solid was collected by filtration, washed with ether and dried in vacuo over phosphorus pentoxide to give potassium DL-β-(N-methoxycarbonyl propen-2-yl) amino-β-cyclohex-1, 4-dienyl propionate [(9.0 g) m.p. 234°-5°, : (found C, 55.6; H, 6.1; N, 4.3; $C_{14}H_{18}KNO_4$ requires C, 55.5; H, 5.9; N, 4.4%). n.m.r. δp.p.m. [(CD$_3$)$_2$SO] 5.67 (H, s); 5.5 (2H, s); 4.25 (H, s); 3.85 (H, m); 3.5 (3H, s); 2.6 (6H, m); 1.85 (3H, s), i.r. $\gamma_{max}$ (KBr) 1640 (CO), 1600 (C=C), 1580 cm$^{-1}$ (CO).

The N-protected amino acid (3.5 g) was suspended in dry acetone (30 ml.), chilled to −10° and treated with ethyl chloroformate (1.08 g) and one microdrop of N-methyl morpholine with stirring. The mixture was maintained at −10° for 30 minutes, chilled to −30°, filtered through kieslguhr and added to a vigorously stirred solution of triethylammonium 6-aminopenicillanate (3.16 g) in 50% aqueous acetone (60 ml.) at 0°. After stirring for 1 hour with no further external cooling the acetone was removed under reduced pressure, the concentrate covered with ethyl acetate (30 ml.) and adjusted to pH 1.5, with stirring, by the addition of concentrated hydrochloric acid at 5° for 20 minutes. After separation of the phases the aqueous layer was readjusted to pH 6.0 with triethylamine and evaporated to dryness under reduced pressure. The white residue was dried over phosphorus pentoxide for 24 hours, thoroughly digested with methylene dichloride (200 ml.) filtered to give the penicillin, [(1.8 g) m.p. 165 (d), n.m.r. δp.p.m. [(CD$_3$)$_2$SO] 6.5 (3H, s); 5.8 (3H, s); 5.35 (2H, s); 4.05 (H, s) 3.85 (H, t); 2.75 (6H, m); 1.5 (6H, d) i.r. $\gamma_{max}$(mull) 3400 (HN); 1770 (lactam CO), 1665 (amide CO), 1580 (CO).].

The material, when subjected to paper chromatography revealed a single zone of inhibition at R$_f$ 0.26 and was estimated to be 75% pure by colorimetric assay with hydroxylamine.

EXAMPLE VI

Preparation of 6-[DL-2-amino (cyclohex-3-en-1-yl) propionamido]penicillanic acid DL-β-amino-β-cyclohex-3-enyl propionic acid hydrochloride, [(42 g) m.p. 197°-198° : (found C, 52.0; H, 7.7; N, 7.0; $C_9H_{16}ClNO_2$ requires C, 52.2; H, 7.7; N, 6.8%) n.m.r. (CD$_3$)$_2$SO] δp.p.m. 8.3 (3H, m); 6.6 (2H, s); 3.35 (H, m); 2.75 (2H, d); 2.0 (7H, m) i.r. $\delta_{max}$ (mull) 2600 and 1940 (NH$^+$), 1710 (CO) 1600 cm$^{-1}$ (C=C)], was prepared exactly as described inExample (IV) when cyclohexane-1-aldehyde was replaced by cyclohex-3-ene-1-aldehyde (55 g).

The amino acid hydrochloride (9.0 g) was added to a solution of sodium ethoxide [prepared from sodium (2.1 g) and absolute ethanol (100 ml.)] in ethanol. Methylacetoacetate (5.5 g) was then added, the mixture refluxed for 16 hours and filtered. The filtrate was concentrated under reduced pressure and triturated with dry diethyl ether. The white solid was collected, washed with dry ether and dried in vacuo over phosphorus pentoxide at 60° for 24 hours, to give sodium-β-(N-methoxycarbonyl propen-2-yl) amino-β-cyclohex-3-enyl propionate [(9.0 g) m.p. 114°-115° : (found C, 53.2; H, 6.9; N, 4.3; $C_{14}H_{20}NaNO_4.H_2O$ requires C, 54.8; H, 7.1; N, 4.5%) n.m.r. δp.p.m. [(CD$_3$)SO] 4.0 (H, d); 5.78 (2H, s); 4.25 (H, s) 3.6 (H, m); 3.5 (3H, s); 2.2 (2H, m); 1.9 (11H, m), i.r. $\gamma_{max}$ (KBr) 1640 (CO), 1580 cm$^{-1}$ (CO$_2^-$).

The penicillin, [(1.1 g) m.p. 160°(d), n.m.r. δp.p.m. [(CD$_3$)$_2$ SO + D$_2$O] 5.7 (2H, s); 5.4 (2H, s); 4.1 (H, s); 3.5 (H, t); 2.7 (2H, m); 2.0-1.5 (13H, m), i.r. $\gamma_{max}$ (KBr) 1760 (lactam CO), 1650 cm$^{-1}$ (amide CO)] was prepared and isolated exactly as described in the latter part of Example V when the N-protected amino acid (2.8 g) was utilised. This material, upon paper chromatography revealed a single zone of R$_f$ 0.43 and was estimated by colorimetric assay with hydroxylamine to be 84% pure.

EXAMPLE VII

Preparation of 6-[DL-2-amino (cyclohex-1-en-1-yl) propionamido]penicillanic acid β-amino-β-cyclohex-1, 4-dienyl propionic acid hydrochloride (6.2 g), dissolved in 5N hydrochloric acid (100 ml.) was hydrogenated under slight positive pressure at room temperature with prehydrogenated 5% palladium on carbon (15 g). After 40 minutes, when the rate of hydrogenation had lessened the reaction was stopped, filtered through kieslguhr and evaporated to dryness under reduced pressure. The white solid, DL-β-amino-β-cyclohex-1-enyl propionic acid [(6.0 g) m.p. 162°-163° n.m.r. δp.p.m. [(CD$_3$)$_2$SO] 5.9 (H, s); 3.85 (H, t); 2.75 (2H, d); 2.0-1.5 (8H, m) i.r. $\gamma_{max}$ (mull) 2600 and 1940 (NH), 1720 (CO), 1600 cm$^{-1}$ (C=C)] was identified as its hydrochloride.

Sodium-β-(N-methoxy carbonyl propen-2-yl) amino-β-cyclohex-1-enyl propionate [(10.1 g) m.p. 124°-126°: (found C, 54.8; H, 7.2; N, 4.5; $C_{14}H_{20}NaNO_4.H_2O$ requires C, 54.8, H, 8.1, N, 4.5%) n.m.r. [(CD$_3$)$_2$SO] δp.p.m. 8.9 (H, d); 5.5 (H, s); 4.3 (H, s); 3.7 (H, m); 3.5 (3H, s); 2.2 (2H, m); 2.0-1.5 (11H, m), i.r. $\gamma_{max}$ (mull) 1640 (CO), 1580 cm$^{-1}$ (CO$_2^-$)] was prepared as described in Example VI except the product crystallised out upon cooling the reaction mixture.

The penicillin, [(1.6 g) m.p. 170 (d), n.m.r. δp.p.m. [(CD$_3$)$_2$SO + D$_2$O] 5.8 (H, s); 5.4 (2H, s); 4.6 (H, s); 3.8 (H, m); 2.8 (2H, m); 2.0-1.5 (14H, m), i.r. $\gamma_{max}$ (mull 1770 (lactam CO), 1660 (amide CO), 1590 cm$^{-1}$ CO$_2^-$)], was prepared and isolated exactly as detailed in Example VI. The product, when subjected to paper chromatography indicated a single zone of inhibition at R$_f$ of 0.42 and was estimated to be 56% pure by colorimetric assay with hydroxylamine.

EXAMPLE VIII

6-[DL-2-amino-2-methyl butyramido]penicillanic acid 3-amino-3-methyl butyric acid (3.0 g) was suspended in dry methylene dichloride (50 ml.) and dry hydrogen chloride passed for 25 minutes at 0°-5° C. Phosphorus pentachloride (6.9 g) was added portion wise over 5 minutes with continuous stirring and the exclusion of moisture. A pale yellow solution was quickly obtained. After 1.5 hours, dry acetone (5 ml.) was added and after 30 minutes the reaction mixture was evaporated to dryness under reduced pressure. Dry toluene (3 × 10 ml.) was added and re-evaporated under reduced pressure. The resultant white solid was triturated with dry diethyl ether, collected by filtration in a dry box and after drying in vacuo over phosphorus pentoxide gave the acid chloride hydrochloride [i.r. $\gamma_{max}$ (mull) 2070 (NH$^+$), 1780 cm$^{-1}$ (CO)].

A cooled suspension of the acid chloride hydrochloride in methylene dichloride (70 ml.) and methylamine (3.5 ml.) were added concurrently over 5 minutes to an ice-cold solution of triethylammonium 6-amino penicillanate (8.13 g) in dry methylene chloride (35 ml.). After stirring for 45 minutes, the white solid was collected by filtration, well washed with methylene dichloride and dried in vacuo over phosphorus pentoxide to give the penicillin [(7.0 g) n.m.r. δp.p.m. (D$_2$O + NaHCO$_3$) 6.55 (2H, m); 4.25 (H, s); 2.7 (2H, s); 1.63–153 (6H, s); 1.45 (6H, s) i.r. $\gamma_{max}$ (mull) 1770 cm$^{-1}$ (lactam CO)]. This material, when subjected to paper chromatography indicated an R$_f$ value of 0.16 and was estimated by colorimetric assay with hydroxylamine to be 67% pure.

EXAMPLE IX

Preliminary in vitro testing of 6-[(1-amino-cyclohexyl) acetamido]penicillanic acid (XI):

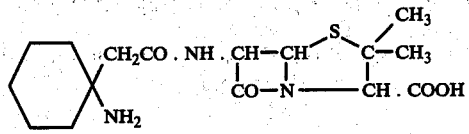

show it to have the same type of antibacterial spectrum as amplicillin. Although it was slightly less active than ampicillin against most strains of bacteria, it was considerably more active than cyclocillin (IV). Moreover, 6-[(1-amino-cyclohexyl) acetamido] penicillanic acid (XI) gave appreciably better blood levels than ampicillin when both compounds were given by mouth at 100 mg./kg. to squirrel monkeys:

|  | AVERAGE SERUM CONCNS.(μg/ml) | | | | |
|---|---|---|---|---|---|
|  | ½ hr. | 1 hr. | 2 hr. | 4 hr. | 6 hr. |
| Compound(XI) | 14.65 | 19.9 | 13.7 | 4.6 | 0.87 |
| Ampicillin | 6.5 | 11.1 | 4.0 | 1.2 | 0.4 |

EXAMPLE X

Preliminary blood level studies of 6-[DL-2-amino-3-methyl butyl carbamido]-penicillanic acid (X) when given by mouth at 100mg/kg to squirrel monkeys showed that higher and more prolonged blood levels could be achieved than with ampicillin.

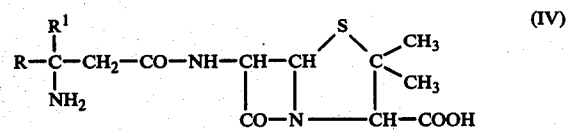

Results

|  | AVERAGE SERUM CONCNS. (μg/ml) | | | | |
|---|---|---|---|---|---|
|  | ½ hr. | 1 hr. | 2 hr. | 4 hr. | 6 hr. |
| Compound (X) | 16.8 | 32.1 | 28.0 | 20.3 | 4.8 |
| Ampicillin | 10.1 | 8.1 | 4.7 | 2.1 | 0.45 |

EXAMPLE XI

The following Table records the blood levels achieved when two more of the compounds of this invention were given by mouth at 100 mg/kg to squirrel monkeys. The results achieved with ampicillin are included for comparison purposes.

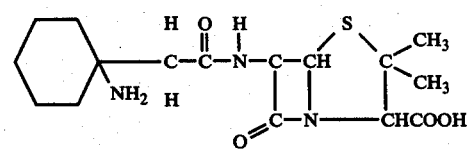

| Compound | Mean conc. μg/ml at hours after dosing | | | | |
|---|---|---|---|---|---|
|  | 0.5 | 1.0 | 2.0 | 4.0 | 6.0 |
| (IV): R = cyclohexyl, R$^1$ = H | 12.2 | 18.7 | 15.9 | 5.9 | 2.0 |
| (IV): R = phenyl, R$^1$ = H | 5.8 | 7.1 | 6.1 | 2.6 | 1.3 |
| Ampicillin | 6.6 | 12.9 | 5.0 | 1.9 | 0.8 |

These results when taken together with the results recorded in Examples (IX) and (X) show that the compounds of this invention are generally better absorbed and/or give more prolonged blood levels in squirrel monkeys than ampicillin. In addition, from these results it appears that compounds of formula (IV) where R and R$^1$ contain no unsaturation are better absorbed than compounds where R or R$^1$ is an unsaturated group.

We claim:

1. A penicillin of the formula

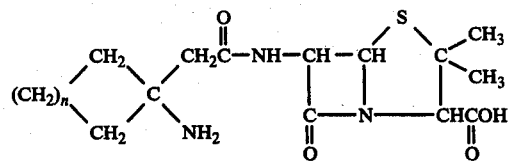

or a non-toxic pharmaceutically acceptable salt or in vivo hydrolysable ester thereof, in which formula R and R$^1$ taken together with the carbon atom to which they are attached form a cyclopentyl, cyclohexyl or cycloheptyl ring.

2. A compound having the formula:

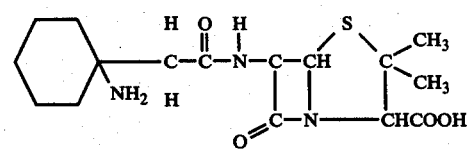

3. A compound of the formula:

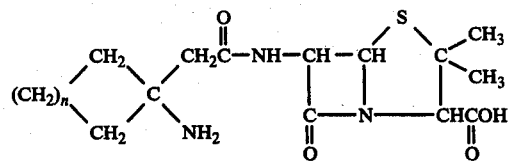

wherein n is 2, 3, or 4, and the non-toxic, pharmaceutically acceptable acid addition salts thereof.

4. A compound of the formula:

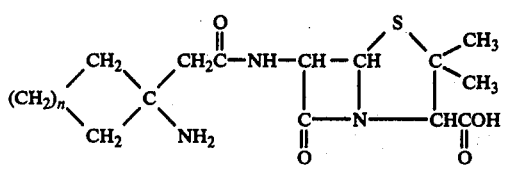

wherein *n* is 2, 3, or 4, and the non-toxic pharmaceutically acceptable salts thereof.

5. The compound

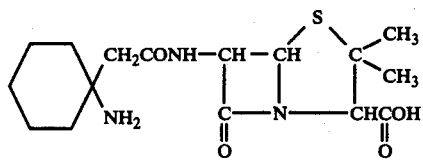

or a non-toxic pharmaceutically acceptable salt thereof.

6. The compound

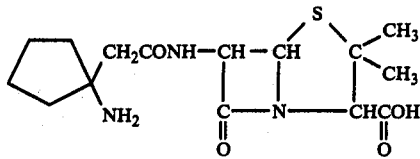

or a non-toxic pharmaceutically acceptable salt thereof.

7. The compound

[structure]

or a non-toxic pharmaceutically acceptable salt thereof.

8. The compound of 6-[DL-2-amino(cyclohexan-1-yl)-propionamido]-penicillanic acid.

9. The compound 6-[DL-2-amino (cyclohex-1,4-dien-1-yl)propionamido]-penicillanic acid.

10. The compound 6-[DL-2-amino(cyclohex-3-en-1-yl)propionamido]-penicillanic acid.

11. The compound 6-[DL-2-amino(cyclohex-1-en-1-yl)propionamido]-penicillanic acid.

* * * * *